United States Patent [19]

Noji et al.

[11] Patent Number: 5,041,106
[45] Date of Patent: Aug. 20, 1991

[54] NEEDLE DEVICE FOR INFUSION

[75] Inventors: Yukio Noji, Shobara; Minoru Iwata, Miyoshi; Hideyuki Yamashita, Shimane, all of Japan

[73] Assignee: Japan Medical Supply Co., Ltd., Hiroshima, Japan

[21] Appl. No.: 484,837

[22] Filed: Feb. 26, 1990

[30] Foreign Application Priority Data

Feb. 28, 1989 [JP] Japan .................................. 1-48244

[51] Int. Cl.⁵ .............................................. A61M 5/32
[52] U.S. Cl. .................................... 604/411; 604/405; 604/126; 604/256
[58] Field of Search ............... 604/264, 411, 403, 405, 604/406, 412, 424, 905, 126, 272, 251, 252, 255–256, 127

[56] References Cited

U.S. PATENT DOCUMENTS

| | | | |
|---|---|---|---|
| 3,662,752 | 5/1972 | Yokoyama | 604/411 |
| 3,783,895 | 1/1974 | Weichselbaum | 604/405 |
| 3,797,521 | 3/1974 | King | 604/405 |
| 3,822,700 | 7/1974 | Pennington | 604/414 |
| 3,993,068 | 11/1976 | Forbery | 604/251 |
| 4,211,588 | 7/1980 | Raines | 604/405 |
| 4,262,671 | 4/1901 | Kersten | 604/411 |
| 4,787,898 | 11/1988 | Raines | 604/411 |
| 4,857,068 | 8/1989 | Kahn | 604/405 |
| 4,959,053 | 9/1990 | Jang | 604/411 |

FOREIGN PATENT DOCUMENTS

| | | | |
|---|---|---|---|
| 51-36400 | 10/1976 | Japan . | |
| 60-30232 | 3/1985 | Japan . | |
| 60-30233 | 3/1985 | Japan . | |
| 2105695 | 3/1983 | United Kingdom | 604/411 |

Primary Examiner—C. Fred Rosenbaum
Assistant Examiner—Kathleen A. Daley
Attorney, Agent, or Firm—Cushman, Darby & Cushman

[57] ABSTRACT

An improved infusion needle device of the type including a liquid delivering passage and an air introducing passage extending in parallel with each other includes a tubular needle, a bottom portion into which the rear part of the tubular needle is immovably fitted, a flange portion made integral with the bottom portion, a cover member airtightly secured to the flange portion and a valve disc received beneath a circular projection on the flange-shaped part of the cover member. As air enters through an air inlet port on the flange portion, the valve disc is raised up so that air is introduced into the interior of the parenteral liquid container via a cutout on the circular projection, a clearance between the bottom portion and the cover member and an annular clearance between the tapered foremost end of the cover member and the tubular needle. When liquid in the container flows out through the air inlet port, the valve disc comes in the inside wall surface of the flange portion under the effect of the dead weight of the liquid itself to close the air inlet port with the valve disc.

6 Claims, 1 Drawing Sheet

NEEDLE DEVICE FOR INFUSION

BACKGROUND OF THE INVENTION

1. Technical Field of the Invention

The present invention relates generally to a needle device for a so-called infusion set with which parenteral liquid is infused into a human body. More particularly, the present invention relates to an improvement of an infusion needle device of the type including a liquid delivering passage and an air introducing passage extending in parallel with each other.

2. Description of the Prior Art

In general, a parenteral liquid infusion set is constructed such that a needle device is provided at one end for allowing a tubular needle to be pierced into the interior of a parenteral liquid container and a vein needle is provided at the other end for allowing a patient's vein to be pierced. In addition, the infusion set includes a drip chamber and a flexible tube extending between the needle device and the vein needle. The conventional needle devices required for the infusion set are classified into two types, i.e., one type including only a liquid delivering passage with an air introducing passage being provided separately and the other type including a liquid delivering passage and an air introducing passage extending in parallel with each other. A few examples of the needle device of the last-mentioned type are disclosed in official gazettes as Japanese Published Utility Model NO. 36400/1976, Japanese Laid-Open Utility Model NO. 30232/1985 and Japanese Laid-Open Utility Model NO. 30233/1985. Specifically, the needle device disclosed in Japanese Published Utility Model NO. 36400/1976 involves a needle tube divided into two passages, one serving as a liquid delivering passage and the other serving as an air introducing passage. The needle device disclosed in Japanese Laid-Open Utility Model NO. 30232/1985 involves a needle tube is formed with a longitudinally extending groove on the side wall thereof so as to allow the groove to serve as an air introducing passage.

Further, the needle device disclosed in Japanese Laid-Open Utility Model NO. 30233/1985 involves a needle tube contoured in a double walled structure so that the inner passage serves as a liquid delivering passage and the outer passage serves as an air introducing passage. Normally, the air introducing passage is fitted with a filter for preventing dust and bacteria in the air from being introduced into the interior of a container. Lately, the filter has been molded of hydrophobic material such as polytetrafluoroethylene resin or the like resin so to prevent liquid in the container from flowing back to the outside.

A needle device of the type including a liquid delivering passage and an air introducing passage extending in parallel with each other can be easily used, but it has several problems in that it is bulky and complicated in structure, resulting in increased production costs. With the needle devices which include an air introducing passage fitted with a filter made of hydrophobic material, if the liquid contains a surface active agent there arises the problem that the liquid is liable to gradually permeate through the filter. Another problem is that once the filter is filled with liquid, air permeates therethrough with much difficulty.

SUMMARY OF THE INVENTION

The present invention has been made with the foregoing background in mind and its object resides in providing an infusion needle device of the type which includes a liquid delivering passage and an air introducing passage extending in parallel with each other wherein the device is simple in structure, has smaller dimensions and can easily be produced at inexpensive cost.

Another object of the present invention is to provide an infusion needle device of the type which includes a liquid delivering passage and an air introducing passage extending in parallel with each other, wherein the device assures that liquid does not undesirably flow or leak to the outside.

To accomplish the above objects, the present invention provides a needle device of the type including a liquid delivering passage and an air introducing passage extending in parallel to each other and having a structure which solves the problems of the conventional device. More particularly, the device comprises a tubular needle, the foremost end of which is sharpened, which serves as the liquid delivering passage. The device further includes a bottom portion into which the rear part of the tubular needle is firmly fitted, a flange portion made integral with the bottom portion, the flange portion being formed with an air inlet port which is covered with an air permeable sheet, and a cover member in which the rear part of the tubular needle and the bottom portion are received with a clearance held therebetween, respectively. The cover member is airtightly secured to the flange portion, and the fore part of the cover member is tapered while defining an annular clearance between the inner wall thereof and the tubular needle. The annular clearance serves as the air introducing passage. The device further includes a valve disc of elastomeric material placed on the inside wall surface of the flange portion, the valve disc being received beneath a circular projection of the flange-shaped part of the cover member and the disc being pressed down slightly by the circular projection. Part of the circular projection is cut out to define an air passage. Thus, there is no barrier to air flow with one cutout, but the circular projection may be provided with more than one cutout.

As air enters through the air inlet port, the valve disc is raised up so that air is introduced into the interior of a parenteral liquid container via the cutout on the circular projection, a groove on the inside wall surface of the flange portion, a clearance between the cover member and the rear portion of the tubular needle and an annular clearance between the foremost tapered end of the cover member and the tubular needle.

When liquid in the container flows out via the air inlet port, the valve disc is brought in close contact with the inside wall surface of the flange portion under the effect of the dead weight force of the liquid itself to close the air inlet port with the valve disc while preventing the liquid from flowing out through the air inlet port.

It is preferable that the flange portion is airtightly secured to the cover member by welding or by using an adhesive.

Other objects, features and advantages of the present invention will be readily apparent from the following description and with reference to the accompanying drawings.

BRIEF DESCRIPTION OF THE DRAWINGS

The present invention is illustrated in the following drawings in which.

DESCRIPTION OF THE PREFERRED EMBODIMENT

Now, the present invention will be described in detail hereinafter with reference to the accompanying drawings which illustrate a preferred embodiment thereof.

Figure 1:
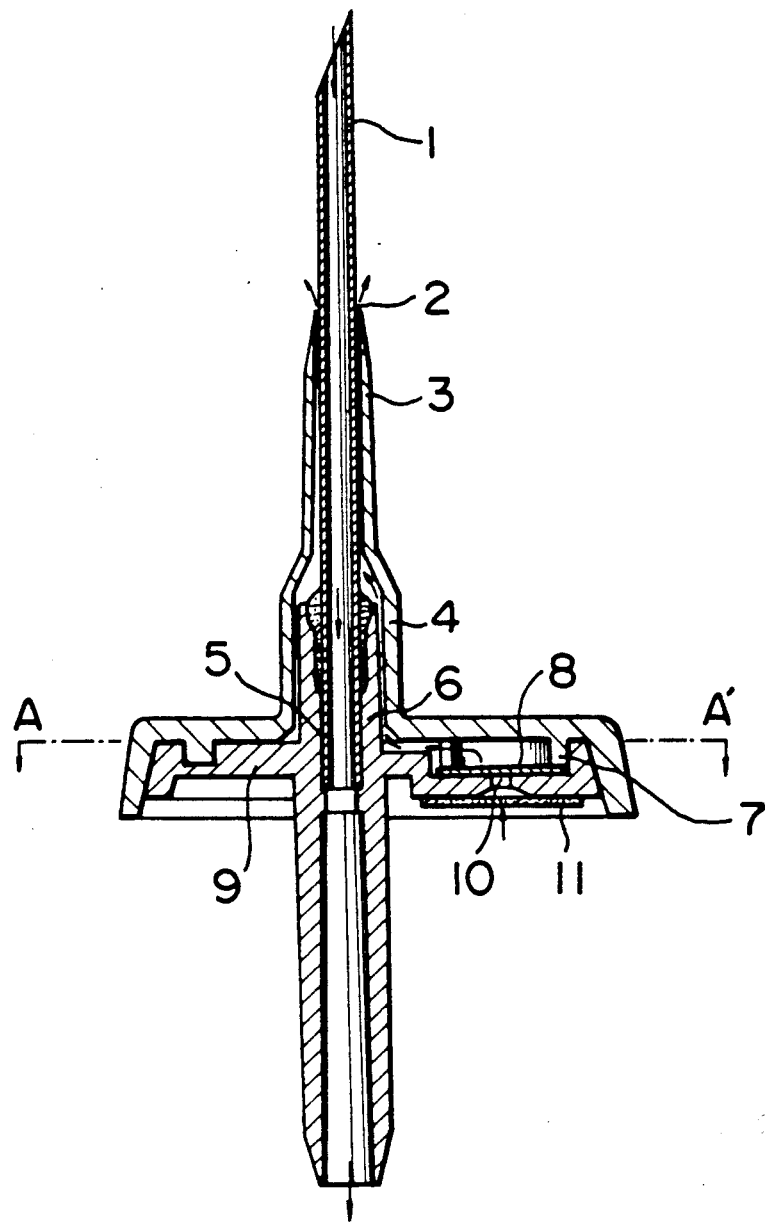
FIG. 1 is a sectional view of an infusion needle device in accordance with an embodiment of the present invention.

FIG. 1 is a sectional view of a needle device in accordance with an embodiment thereof.

As will be apparent from the drawing, the needle device of the present invention includes a tubular needle 1, a needle bottom portion 6, a cover portion 4 and a valve disc 8. The tubular needle 1 is sharpened so as to allow its foremost portion to be pierced into a rubber stopper. In the illustrated embodiment, the foremost portion of the tubular needle 1 is formed with an opening at the foremost end thereof like an injection needle. Alternatively, the foremost end of the tubular needle 1 may be kept closed but the needle 1 may be formed with an opening on the side wall thereof.

This arrangement prevents a part of the rubber stopper from being cut off by a piercing operation of the needle 1. The rear end part of the tubular needle 1 is firmly held by the bottom portion 6 using an adhesive.

The bottom portion 6 is made integral with a flange 9 at a substantially middle part therof and an air inlet port 10 is formed on the flange 9. An air permeable sheet 11 is adhesively attached to the outer surface of the flange 9 to cover the air inlet port 10 therewith, and the valve disc 8 is placed inside of the air inlet port 10. Any material is employable for the air permeable sheet 11, if it is proven that it prevents dust and bacteria in the air from passing therethrough. Generally, it is preferable to use paper or nonwoven fabric for the air permeable sheet 11 from the viewpoint of strength, productivity and cost. The air permeable sheet 11 can be attached around the circular edge of the air inlet port 10 by welding the peripheral edge of the air permeable sheet 11 or by using an adhesive. The valve disc 8 is molded of flexible material such as rubber, soft synthetic resin or the like and it is particularly preferable to employ silicone rubber as material for the valve disc 8. The valve disc 8 is preferably designed in the form of a circular disc but the contour of the valve disc 8 need not be limited only to this shape. Alternatively, other suitable contours may be employable. Usually, the thickness of the valve disc should be in the range of 0.2 to 0.8 mm.

The cover member 4 is designed to surround the rear end part of the tubular needle 1 and the front side of the flange 9 and it is airtightly secured around the periphery of the flange 9. As is apparent from FIG. 1, the fore part of the cover member 4 is tapered to facilitate piercing of the foremost end of the cover member 4 into a container, and an annular fine clearance is formed between the tubular needle 1 and the inner wall of the tapered part of the cover member 4 so as to allow air to flow therethrough. In addition, an annular clearance is provided between the bottom portion 6 of the tubular needle 1 and the cover member 4 so that air is introduced into the container via the air inlet port 10 and the foregoing annular clearances.

Figure 2:
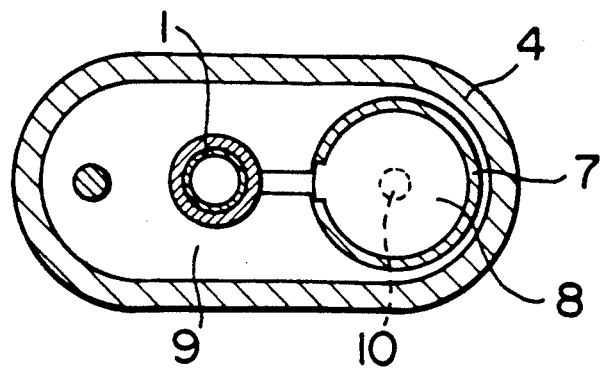
FIG. 2 is a cross-sectional view of the needle device taken in line A—A' in FIG. 1.

As is best seen in FIG. 2 which is a sectional view of the needle device taken in line A—A' in FIG. 1, the cover member 4 is formed with a circular projection 7 in which a part of the valve disc 8 is received. The circular projection 7 is cut out at the left-hand part as seen in FIG. 2 so that the annular clearance between the cover member 4 and the bottom portion 6 is communicated with the cutout of the circular projection 7 via a groove on the inside wall of the cover member 4.

Normally, air which has entered through the inlet port 10 lifts up the valve disc 8 to create a clearance between the valve disc 8 and the inside wall of the flange 9, whereby it flows into the interior of the needle device via the thus created clearance. If it happens that liquid in the container flows down against the air flow, it depresses the valve disc 8 on the inside wall surface of the flange 9 under the effect of the gravity force of the liquid itself to close the inlet port 10 with the valve disc 8. Consequently, the valve disc 8 prevents the liquid from flowing out through the inlet port 10 via the cutout of the circular projection 7. If this cutout is excessively narrow, air flowing is obstructed. On the contrary, if it is excessively wide, the valve disc 8 is held unstably. Thus, the size of the cutout should preferably be determined in the range of 5 to 180 degrees in terms of an angle as seen from the center of the circular projection 7. Thus, there is no barrier to air flow with one cutout, but the circular projection may be provided with more than one cutout. In the case where there are a number of cutouts, the total angle from each of the cutouts should be in said range.

As mentioned above, the cover member 4 is airtightly secured to the flange 9. It is preferable that this airtight securing be accomplished by welding or by using an adhesive. Particularly, it is most preferable that airtight securing is accomplished by employing a supersonic welding process.

The needle device of the present invention is practically useful when an infusion set or a drip chamber is connected to the rear end of the needle device.

When the needle device is put in practical use, the tubular needle 1 and the tapered fore end of the cover member 4 are pierced into the interior of a parenteral liquid container through a rubber stopper. Liquid in the container flows out from the rear end of the bottom portion 6 through the interior of the tubular needle 1, while air is introduced into the interior of the container via the air permeable sheet 11, the air inlet port 10, the clearance between the valve disc 8 and the inside wall of the flange 9 and the annular clearance 2 between the tubular needle 1 and the foremost end of the cover member 4.

Usually, the tubular needle 1 is made of metallic material, e.g., stainless steel. Alternatively, it may be made of hard synthetic resin. It is preferable that the bottom portion 6 and the cover member 4 are molded of synthetic resin by employing an injection molding process. Since both members are simple in cofiguration, there is no need of using a split mold assembly, and a number of members can simultaneously be molded using a single mold. Polypropylene, ABS resin, polyethylene and polycarbonate can be used as typical synthetic resins for molding the bottom portion 6 and the cover member 4.

Since the needle device of the present invention is simple in structure and can be produced on a mass production line, it can be designed in smaller dimensions and produced at low cost. Thus, it can preferably be used as a disposable type medical instrument. In addition, since it is equipped with a reverse flow preventive valve, there is no danger that liquid in a parenteral liquid container leaks out from the air inlet port. Consequently, it can safely be used for any kind of parenteral liquid.

While the present invention has been described above with respect to a single preferred embodiment thereof, it should of course be understood that it should not be limited only to this but various changes or modifications may be made without departure from the scope of the present invention as defined by the appended claims.

What is claimed is:

1. A needle device of the type including a liquid passage and an air passage, said needle device comprising:
    a tubular needle having one end sharpened to facilitate introduction of said tubular needle into a liquid container, said tubular needle forming a portion of the liquid passage along its longitudinal axis;
    base means having a tube shaped member and a flange member attached perpendicularly at a central portion of said tube shaped member, one end of said tube shaped member being adapted to receive the other end of said tubular needle, said flange member having a through hole formed at its outer periphery, said tube shaped member forming another portion of the liquid passage;
    cover means having a cylindrical member and a flange member attached perpendicularly at one end of said cylindrical member, said cylindrical member surrounding but being spaced from said one end of said tube shaped member and a portion of said tubular needle which extends beyond said one end of said tube shaped member, the other end of said cylindrical member being tapered to facilitate insertion into a liquid container, said flange member of said cover member being adapted to mate with said flange member of said base means and to form a cavity between said flange members which communicates with said through hole, said flange member of said cover means having an annular projection with an opening, said annular projection being disposed concentrically to said through hole in said flange member of said base means when said flange members are mated to each other;
    the air passage being formed by the space between said cylindrical member and said tubular needle, the space between said cylindrical member and said tube shaped member, the cavity formed between the flange members of said cover means and said base means, the at least one opening in said annular projection and the through hole in said flange member of said base means; and
    valve means for opening the air passage to facilitate air flow along the air passage in a forward direction and for closing the air passage to prevent liquid from flowing along the air passage in a reverse direction, said valve means including a disc shaped member having top and bottom sides and being disposed within said annular projection opposite to said through hole, said disc shaped member being moved to a valve open position, away from the through hole, by air pressure incident on the bottom side of the disc shaped member through said through hole and being moved to a closed valve position, against the through hole, by liquid pressure incident on the top side of the disc shaped member from a liquid container.

2. The needle device as in claim 1, wherein the flange members are secured to each other by an adhesive.

3. The needle devce as in claim 1, wherein the flange members are secured to each other by welding.

4. The needle device as in claim 1, said opening in said annular projection ranging from 5° to 180°.

5. The needle device as in claim 1, wherein said annular projection has more than one opening.

6. The needle device as in claim 1, further comprising an air permeable sheet covering said through hole in said base means.

* * * * *